(12) United States Patent
Fan et al.

(10) Patent No.: US 11,337,671 B2
(45) Date of Patent: May 24, 2022

(54) METHODS AND SYSTEMS FOR IMPROVED SPECTRAL FIDELITY FOR MATERIAL DECOMPOSITION

(71) Applicant: GE Precision Healthcare LLC, Milwaukee, WI (US)

(72) Inventors: Jiahua Fan, New Berlin, WI (US); Matthew Getzin, Wauwatosa, WI (US); Sathish Ramani, Niskayuna, NY (US); Peter Edic, Albany, NY (US)

(73) Assignee: GE Precision Healthcare LLC, Milwaukee, WI (US)

( * ) Notice: Subject to any disclaimer, the term of this patent is extended or adjusted under 35 U.S.C. 154(b) by 181 days.

(21) Appl. No.: 16/741,407

(22) Filed: Jan. 13, 2020

(65) Prior Publication Data

US 2021/0212656 A1 Jul. 15, 2021

(51) Int. Cl.
*G01D 18/00* (2006.01)
*A61B 6/00* (2006.01)
(Continued)

(52) U.S. Cl.
CPC .............. *A61B 6/584* (2013.01); *A61B 6/032* (2013.01); *A61B 6/4035* (2013.01);
(Continued)

(58) Field of Classification Search
CPC ..... A61B 6/032; A61B 6/4035; A61B 6/4241; A61B 6/5258; A61B 6/584; A61B 6/583; A61B 6/5205; A61B 6/482; A61B 3/102; A61B 6/488; A61B 6/582; A61B 3/0025; A61B 6/542; A61B 6/544; A61B 6/545; A61B 6/586; A61B 3/14; A61B 6/4085; A61B 6/505; A61B 3/0058; A61B 3/12; A61B 6/504; A61B 5/0066; A61B 6/037; A61B 5/0075; A61B 6/481; A61B 5/055; A61B 5/742; A61B 5/7475; A61B 8/14; A61B 5/7267; A61B 8/12; A61B 6/5217; A61B 8/0891; A61B 6/4042; A61B 6/4441; A61B 6/5235; A61B 6/06; A61B 6/027; A61B 6/405; A61B 6/461; A61B 6/52; A61B 6/48; A61B 6/465; A61B 6/467;
(Continued)

(56) References Cited

U.S. PATENT DOCUMENTS 5,521,955 A * 5/1996 Gohno .................. C12N 9/88
378/18
2014/0321608 A1* 10/2014 Ueki .................... A61B 6/032
378/18
(Continued)

*Primary Examiner* — Irakli Kiknadze
(74) *Attorney, Agent, or Firm* — McCoy Russell LLP

(57) ABSTRACT

Various methods and systems are provided for spectral computed tomography (CT) imaging. In one embodiment, a method comprises performing a scan of a subject to acquire, with a detector array comprising a plurality of detector elements, projection data of the subject, generating corrected path-length estimates based on the projection data and one or more selected correction functions, and reconstructing at least one material density image based on the corrected path-length estimates. In this way, the fidelity of spectral information is improved, thereby increasing image quality for spectral computed tomography (CT) imaging systems, especially those configured with photon-counting detectors.

20 Claims, 7 Drawing Sheets

(51) Int. Cl.
*A61B 6/03* (2006.01)
*G06T 7/00* (2017.01)

(52) U.S. Cl.
CPC .......... *A61B 6/4241* (2013.01); *A61B 6/5258* (2013.01); *G06T 7/0012* (2013.01); *G06T 2207/10081* (2013.01); *G06T 2207/20182* (2013.01); *G06T 2207/30004* (2013.01); *G06T 2211/421* (2013.01)

(58) Field of Classification Search
CPC . G06T 2207/10081; G06T 2207/20182; G06T 2207/30004; G06T 2211/421; G06T 7/0012; G06T 11/005; G06T 11/006; G06T 2211/408; G06T 7/11; G06T 2211/424; G06T 11/008; G06T 2207/30008; G06T 2207/10116; G06T 5/002; G06T 5/50; G06T 2207/20128; G06T 2207/30052; G06T 7/12; G01N 2223/419; G01N 23/046; G01N 2223/206; G01N 2223/401; G01N 23/04; G01N 23/083; G01N 23/18; G01N 33/46; G01N 2223/33; G01N 2223/66; G01N 2223/402; G01N 23/087; G01T 1/1611; G01T 1/16; G01T 1/1615; G01T 1/1642; G01T 1/1647; G01T 1/1648; G01T 1/2985; A61N 7/02; A61C 13/0004; A61C 7/002; A61C 7/08; A61C 7/10; A61C 9/0053; G02B 5/203; G02B 5/32; G03H 1/0248; G03H 1/0486; G03H 1/181; G03H 1/22; G03H 1/24; G03H 1/28; G03H 2001/0489; G03H 2001/0491; G03H 2001/0833; G03H 2001/186; G03H 2001/2278; G03H 2001/2655; G03H 2210/22; G03H 2210/33; G03H 2210/454; G03H 2210/46; H01J 2235/068; H01J 2235/062; H01J 35/045; H01J 35/065; H01J 35/26; H05G 1/32; H05G 1/58; H05G 1/10; G06K 9/6298; G06K 9/6215; A61K 49/04; G06V 10/245; G06V 10/20
USPC .......................................... 378/4, 18, 19, 207
See application file for complete search history.

(56) References Cited

U.S. PATENT DOCUMENTS

| | | | |
|---|---|---|---|
| 2016/0054453 A1* | 2/2016 | Moriyasu | G16H 50/20 |
| | | | 378/19 |
| 2016/0058404 A1* | 3/2016 | Nitta | A61B 6/4241 |
| | | | 382/131 |
| 2019/0251713 A1* | 8/2019 | Chen | G06N 3/084 |
| 2021/0007691 A1* | 1/2021 | Prabhu Verleker | A61B 6/06 |

* cited by examiner

METHODS AND SYSTEMS FOR IMPROVED SPECTRAL FIDELITY FOR MATERIAL DECOMPOSITION

FIELD

Embodiments of the subject matter disclosed herein relate to spectral computed tomography (CT) imaging.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

BRIEF DESCRIPTION

In one embodiment, a method comprises performing a scan of a subject to acquire, with a detector array comprising a plurality of detector elements, projection data of the subject, generating corrected path-length measurements based on the projection data and one or more selected correction functions, and reconstructing at least one material density image based on the corrected path-length measurements. In this way, the fidelity of spectral information is improved, thereby increasing image quality for spectral computed tomography (CT) imaging systems, including those configured with photon-counting detectors.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
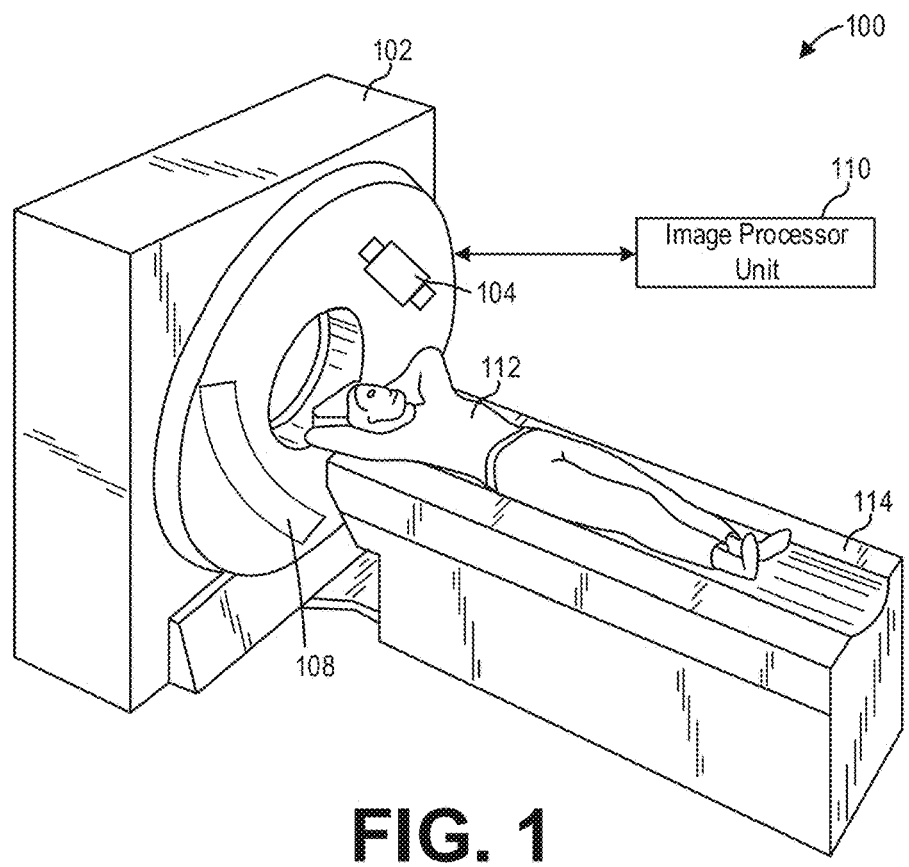
FIG. 1 shows a pictorial view of an imaging system, according to an embodiment.
Figure 2:
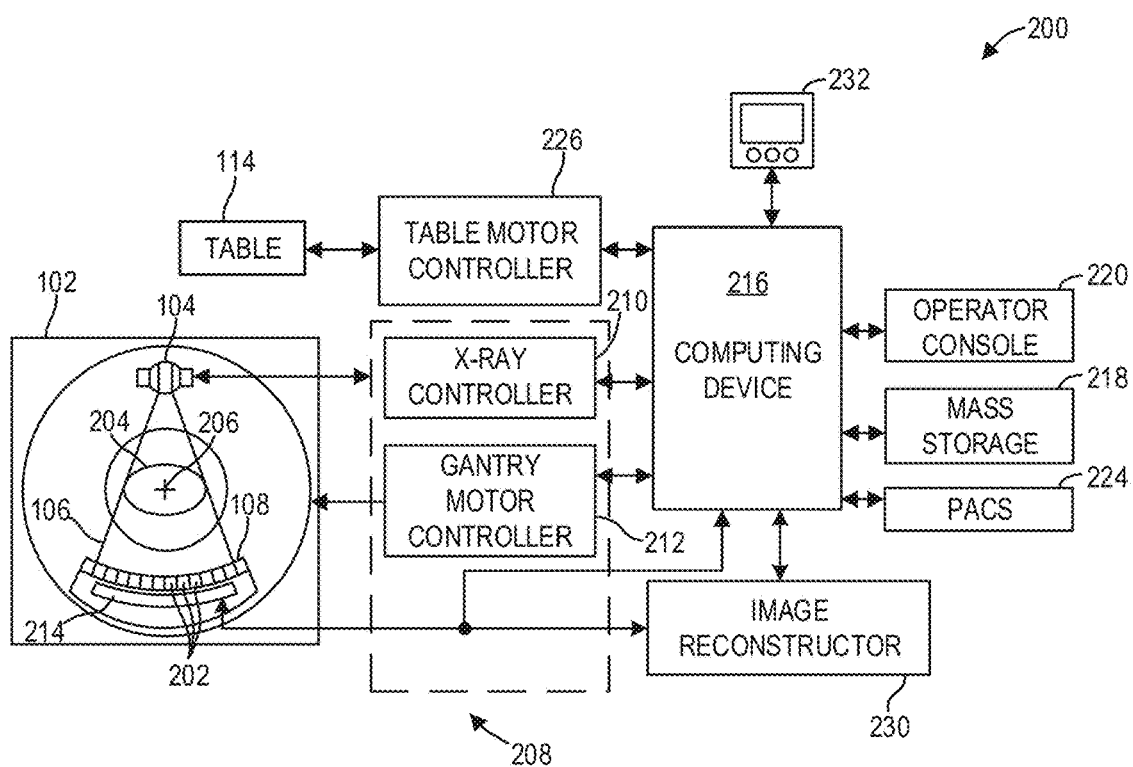
FIG. 2 shows a block schematic diagram of an exemplary imaging system, according to an embodiment.

The following description relates to various embodiments of spectral computed tomography (CT) imaging. In particular, systems and methods for improving spectral fidelity of CT imaging systems are provided. An example of a CT imaging system that may be used to acquire images in accordance with the present techniques is shown in FIGS. 1 and 2. The CT imaging system may be configured with photon-counting detectors, as the additional spectral information and higher image quality are obtainable with such detectors. However, the ability to maintain high spectral fidelity is crucial for accurate data reconstruction and material compositional analysis. For example, the variations in the conversion of photons to measurable or countable electric pulses may have a substantial impact on image quality. Further, as the number of measurements (i.e., energy bins) increases in spectral detectors, for example for dual-energy imaging or multi-energy imaging, the number of conversion efficiency variations also increases, thereby impacting image quality. For example, the accuracy of material density estimation may be substantially affected by low signal-to-noise ratio (SNR) due to different causes, such as low-performing detector elements or detector elements with reduced detection efficiency.

Figure 7:
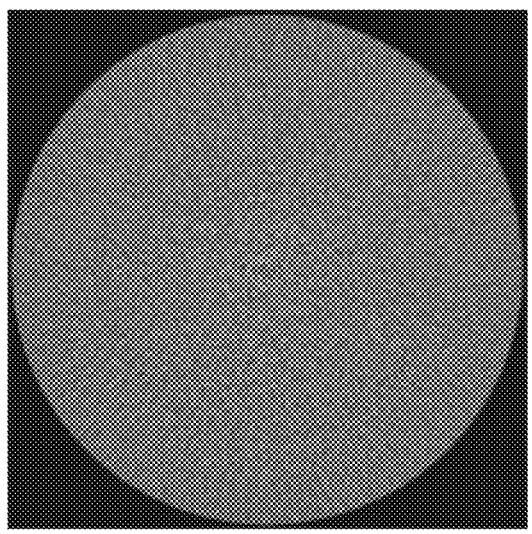
FIG. 7 shows an example image exhibiting ring artifacts due to low-efficiency pixels, according to an embodiment.
Figure 8:
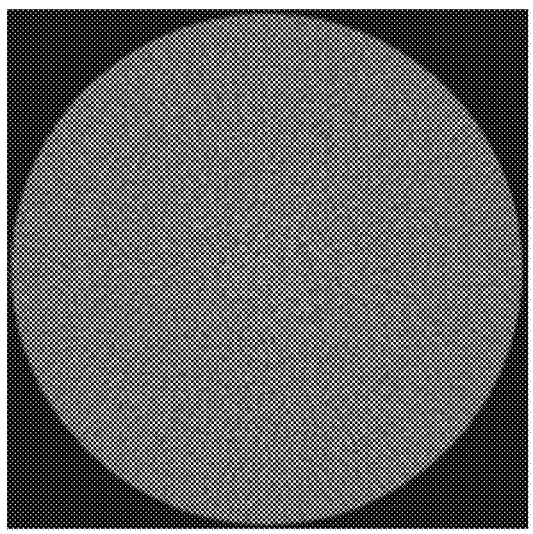
FIG. 8 shows an example image with low-efficiency pixel correction, according to an embodiment.
Figure 9:
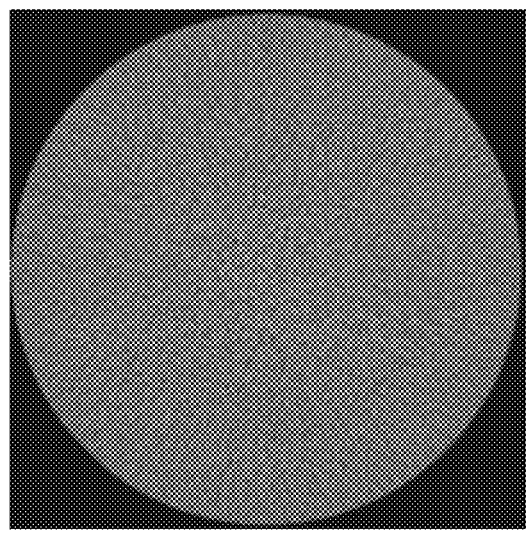
FIG. 9 shows an example image with low-efficiency pixel correction and corrected spectral forward modeling, according to an embodiment.
Figure 10:
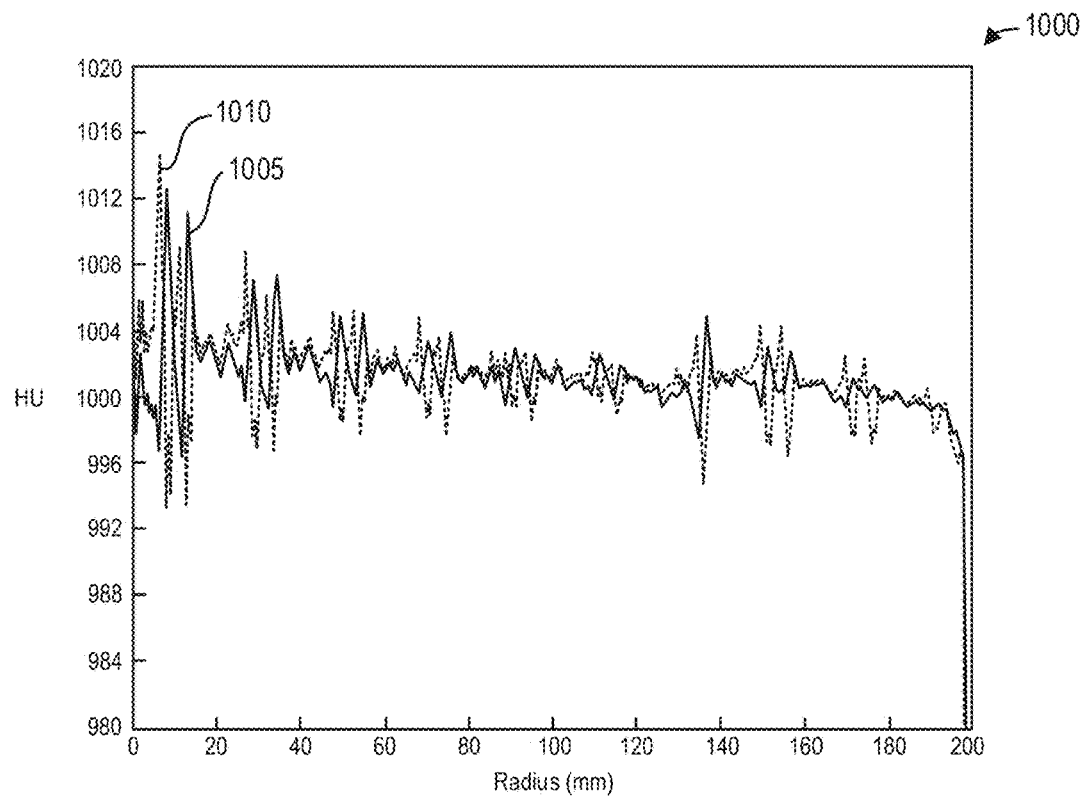
FIG. 10 shows a graph illustrating azimuthally-averaged radial profiles to compare the uncorrected image of FIG. 7 and the partially-corrected image of FIG. 8, according to an embodiment.
Figure 11:
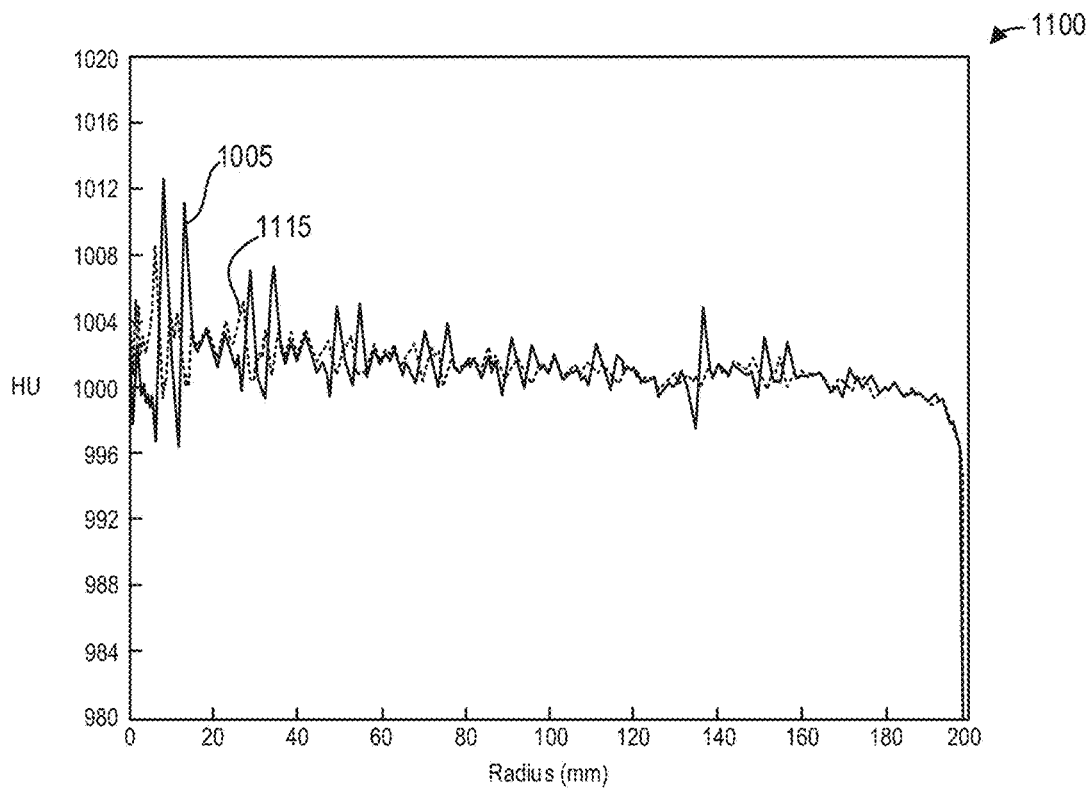
FIG. 11 shows a graph illustrating azimuthally-averaged radial profiles to compare the uncorrected image of FIG. 7 and the fully-corrected image of FIG. 9, according to an embodiment.

Methods and systems are thus provided herein to offset the effects of low SNR regions on image quality, which include improving the spatial and contrast resolution of the imaging system and minimizing detrimental image artifacts. The methods include identifying such regions of underperforming detector pixels or elements, enhancing the signal from such regions, and incorporating the enhanced signal into forward models used in later image chain algorithms, thus reducing or eliminating distortions in acquired spectral information. Such a method, such as the method shown in FIG. 3, includes generating corrected path-length estimates from acquired imaging data and one or more correction functions. In one example method, such as the method shown in FIG. 4, the correction functions may be predetermined to address efficiency and performance issues of the detector elements that may be a function of detector design or other pre-existing detector issues. In other example methods, such as the methods shown in FIGS. 5 and 6, the correction functions may be selected or determined based on dynamic issues with detector performance or efficiency identified from projection data acquired during a scan of an imaging subject. FIGS. 7-9 depict examples of the relative impact of processing projection data or imaging data as described herein, wherein FIG. 7 shows an image without correction, FIG. 8 shows an image with a limited correction, and FIG. 9 shows an image processed with a full correction according to the methods provided herein. The graphs shown in FIGS. 10 and 11 illustrate the impact of the correction method on the example images of FIGS. 7-9.

While a CT imaging system configured with photon-counting detectors is described herein, it should be appreciated that the methods provided herein for improving spectral fidelity may be implemented with CT imaging systems configured with spectral detectors other than photon-counting detectors, and further may be implemented in other modalities that may benefit from enhancing a spectral signal that may be converted with spectral forward modeling without distortion of spectral information.

Turning now to FIG. 1, FIG. 1 illustrates an exemplary CT imaging system 100 configured for CT imaging. Particularly, the CT imaging system 100 is configured to image a subject 112 such as a patient, an inanimate object, one or more manufactured parts, and/or foreign objects such as dental implants, stents, and/or contrast agents present within the body. In one embodiment, the CT imaging system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts only a single x-ray source 104, in certain embodiments, multiple x-ray sources and detectors may be employed to project a plurality of x-ray radiation beams 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at a low operating voltage (low-kVp) and the other at high operating voltage (high-kVp). It should thus be appreciated that the methods described herein may be implemented with single-energy acquisition techniques as well as dual-energy acquisition techniques.

In certain embodiments, the CT imaging system 100 further includes an image processor unit 110 configured to reconstruct images of a target volume of the subject 112 using an iterative or analytic image reconstruction method. For example, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within a volume of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam intensity at the detector location. The attenuation measurements from all the detector elements are acquired separately to produce a transmission profile.

In some CT imaging systems, the x-ray source and the detector array are rotated with a gantry within the imaging plane and around the object to be imaged such that an angle at which the radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans from a volume of the subject or object, a three-dimensional rendering of the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone-beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

FIG. 2 illustrates an exemplary imaging system 200 similar to the CT imaging system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density maps or images comprising each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two or more basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the imaging system 200 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218, either directly or via computing device 216, as shown in FIG. 2. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes (such as the methods described below with reference to FIGS. 3-6) described further herein may be stored as executable instructions in non-transitory memory on a computing device (or controller) in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

In examples wherein the detector elements 202 of the detector array 108 comprise photon-counting detectors, the variations in the conversion of photons to measurable or countable electric pulses may have a substantial impact on image quality. Further, as the number of measurements (i.e., energy bins) increases in spectral detectors, for example for dual-energy imaging or multi-energy imaging, the number of conversion efficiency variations also increases, thereby impacting image quality. For example, the accuracy of material density estimation may be substantially affected by low signal-to-noise ratio (SNR) due to different causes, such as low-performing detector elements 202 in the detector array 108 or detector elements 202 or detector pixels with reduced detection efficiency.

Methods and systems are thus provided herein to offset the effects of low SNR regions on image quality, which include improving the spatial and contrast resolution of the imaging system 200 and minimizing detrimental image artifacts. The methods include identifying such regions of under-performing detector pixels or elements, enhancing the signal from such regions, and incorporating the enhanced signal into forward models used in later image chain algorithms, thus reducing or eliminating distortions in acquired spectral information.

Material discrimination or material decomposition (MD), such as the basis material decomposition technique discussed hereinabove, is achievable because the normalized n-valued vector I containing the processed data from a photon-counting detector element 202 is a function of the number of photons that are emitted from the x-ray source 104 in any given energy distribution $I_0$ and the path length $A_m$ through unknown materials indexed by m. Normalized vector I is generated by taking the ratio of measurements acquired with and without an object present with the x-ray radiation beam 106. Given a calibration method, such as scanning a phantom with a known material composition and precise geometry, a forward model f for mapping the normalized number of photons measured at a detector element or detector pixel as a function of energy, (I; $R^n$), to the same or lower-dimensional hypersurface of path lengths through materials with a known density, (A: $R^m$):

$$(I, A) \rightarrow f,$$

such that the forward model f maps the path lengths, A, to the normalized number of photons measured at a detector element as a function of energy, I:

$$f(A) = I.$$

However, when real diagnostic imaging data is acquired, the only value that is known is the normalized number of measured photons $I_r$ attenuated by the imaging subject (i.e., the patient) rather than the path lengths of materials comprising the imaging subject. The inverse of the forward model f may therefore map the normalized number of measured photons $I_r$ to an estimate of the path lengths, $A_r$:

$$A_r = f^{-1}(I_r),$$

where $f^{-1}$ is the inverse forward model. This approach works well for an ideal detector with perfect detector elements 202 in the detector array 108. However, in practice, some detector elements 202 may perform better or worse than other detector elements 202 in the detector array 108. Any signal distortions in the normalized number of measured photons $I_r$ that are a result of detector pixel efficiency or other counting behaviors, or which are introduced during corrections or initial processing of the normalized number of measured photons $I_r$, will have a strong and potentially negative impact on the approximation accuracy of the estimated path lengths, $A_r$.

A correction for measurements counted with low data fidelity or low efficiency (e.g., low SNR) can be achieved by applying a correction function $g_\Omega$ to the normalized number of measured counts $I_r$ such that:

$$\tilde{I}_r = g_\Omega(I_r),$$

where $\tilde{I}_r$ is the corrected normalized number of measured photon counts and $\Omega$ is the domain of measurements used to generate the correction. However, applying the correction function $g_\Omega$ at the point of measurement alone will result in a mismatch in the detector efficiency and the spectral composition used to create the forward model f and those at the values of $\tilde{I}_r$. In other words, while the inverse forward model $f^{-1}$ may accurately map the normalized number of measured photon counts $I_r$ to path lengths $A_r$ for an ideal detector, the same inverse forward model may not accurately map the corrected normalized number of measured photon counts $\tilde{I}_r$ to corrected estimated path lengths $\tilde{A}_r$:

$$f^{-1}(I_r) = A_r \neq \tilde{A}_r = f^{-1}(\tilde{I}_r).$$

Consequently, any function that is applied to the measurement should be applied in the forward model so that, for each detector pixel or element, the forward model is based on the same detector efficiencies and spectral characteristics of the real measurements.

Figure 3:
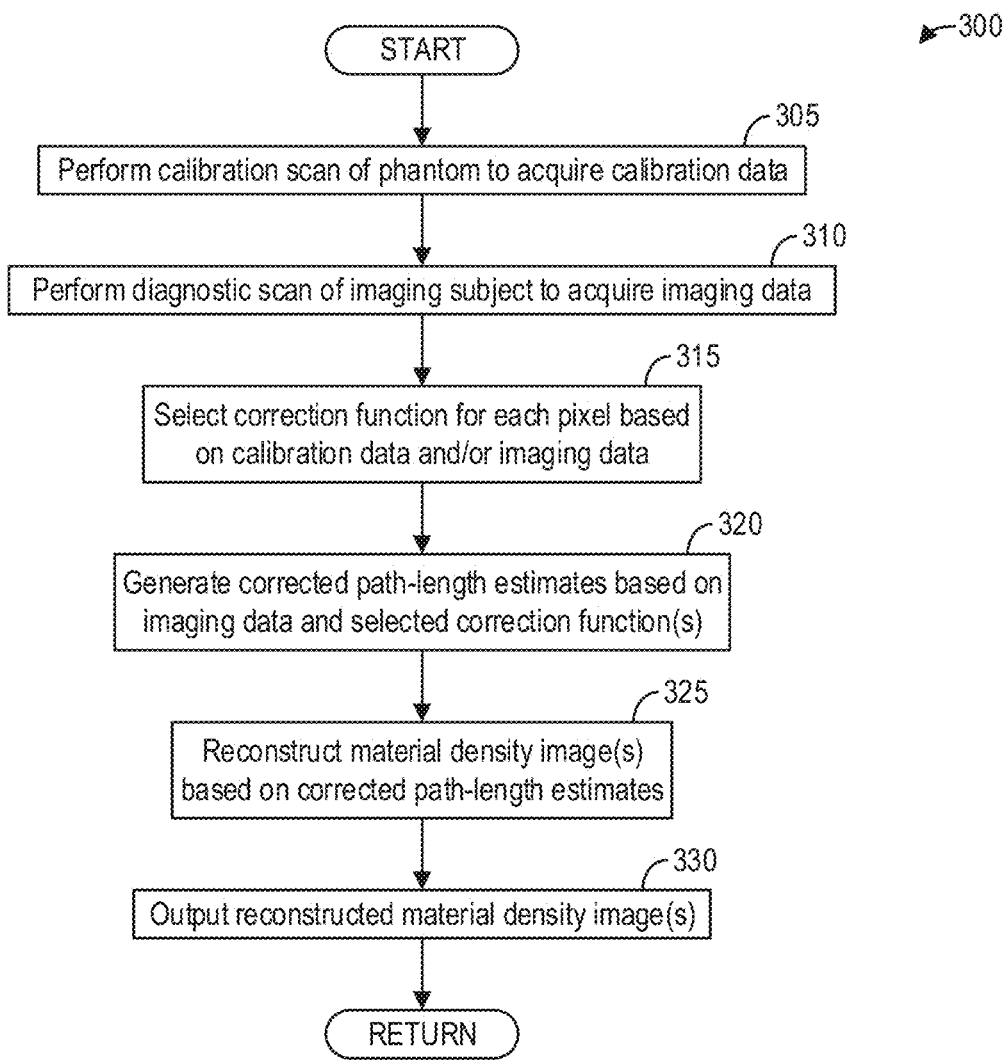
FIG. 3 shows a high-level flow chart illustrating an example method for material decomposition with improved spectral fidelity, according to an embodiment.

As described further herein, methods for improving spectral fidelity for material decomposition are provided that include selecting appropriate correction functions $g_\Omega$ and applying them to accurately enhance the spectral characteristics of measured data. As an illustrative example, FIG. 3 shows a high-level flow chart illustrating an example method 300 for material decomposition with improved spectral fidelity, according to an embodiment. Method 300 is described with regard to the systems and components of FIGS. 1 and 2, though it should be appreciated that the method 300 may be implemented with other systems and components without departing from the scope of the present disclosure. Method 300 may be implemented as executable instructions in the non-transitory memory of the computing device 216 and/or the image reconstructor 230, for example, and may be executed by the computing device 216 and/or the image reconstructor 230 to perform the actions described herein.

Method 300 begins at 305. At 305, method 300 performs a calibration scan of a phantom to acquire calibration data. For example, method 300 may control the x-ray source 104 via the x-ray controller 210 to generate an x-ray radiation beam 106 towards a phantom with a known material composition and a known, precise geometry, and further may acquire, via the DAS 214, projection data corresponding to the detected photons measured or counted by the detector elements 202 of the detector array 108. Data may also be acquired when the phantom is removed from the x-ray radiation beam 106 for normalization purposes. As the material composition and geometry of the phantom is known, the projection data thus acquired comprises calibration data for identifying the spectral characteristics and performance of the detector elements 202, for example.

At 310, method 300 performs a diagnostic scan of an imaging subject to acquire imaging data. For example, method 300 may control the x-ray source 104 via the x-ray controller 210 to generate an x-ray radiation beam 106 towards an imaging subject, such as the subject 204, with an unknown material composition and an unknown geometry, and further may acquire, via the DAS 214, projection data corresponding to the detected photons measured or counted by the detector elements 202 of the detector array 108. The imaging data comprises the projection data thus acquired.

At 315, method 300 selects a correction function, such as a correction function $g_\Omega$, for each detector pixel or detector element based on the calibration data and/or the imaging data. For example, method 300 may analyze the calibration data and/or the imaging data to determine if there is a dynamic performance issue between detector pixels or between scans, such as dynamically low-performance detector pixels, a pixel whose performance may change between or during scans. For example, method 300 may evaluate the efficiency of each detector pixel or detector element 202 based on the calibration data. In some examples, the performance problem may be a function of the detector design such that the issue is repeatable between detectors and between scans with the same detector, and so the correction function may be predefined. An example method that includes addressing or correcting predetermined or pre-existing detector inefficiencies is described further herein with regard to FIG. 4.

In addition to determining whether the correction function $g_\Omega$ is a predetermined or dynamically applied correction function, as well as whether the correction function is a linear or a nonlinear function, method 300 may further select the correction function $g_\Omega$ for each detector element 202 based on the type of detector element problem identified and in what neighborhood domain $\Omega$ the correction function $g_\Omega$ is to be applied. For example, the correction of a single non-functioning detector element 202 may be achieved by a spatial interpolation filter which uses a weighted combination of data from several nearby detector elements 202 within the same row of the non-functioning detector element 202. As another example, a correction function $g_\Omega$ may comprise a nonlinear filter such as a median filter, a neighborhood pooling function at a pixel- or element-level (such as bilateral filtering) or at a patch-level (such as a non-local means). Further, the correction function $g_\Omega$ for a given detector element 202 may be selected to work in a spatial domain (e.g., pooling data across a detector row, across a detector column, over a neighborhood of rows and columns, across pixel depths for a multi-layer detector, and so on), in the time or view domain (e.g., pooling data from nearby time points or viewing angles), or in the spectral domain (e.g., pooling data across energy bins).

The computing device 216 and/or the image reconstructor 230 may therefore be configured with a library of correction functions $g_\Omega$ stored in non-transitory memory that are designed for different scenarios, and method 300 may select, for each detector element 202, an appropriate correction function $g_\Omega$ from said library. For a detector element 202 identified as properly functioning, method 300 may select a correction function $g_\Omega$ for the properly-functioning detector element 202 that comprises an identity function (i.e., a function that returns the same value that was used as its argument) so that the signal for the detector element 202 is unchanged.

After selecting a correction function for each detector element, method 300 continues to 320. At 320, method 300 generates corrected path-length estimates based on the imaging data and the selected correction function(s). As mentioned hereinabove, merely applying the correction function $g_\Omega$ for a given detector element 202 to the signal acquired by the detector element 202 may not sufficiently enhance the spectral fidelity of the detector element 202. Thus, in examples wherein the performance deficiencies are predetermined, method 300 may apply the correction function to the calibration data to obtain corrected calibration data, generate a corrected forward model based on the corrected calibration data, correct the acquired imaging data with the correction function, and convert the corrected imaging data with the inverse of the corrected forward model to obtain the corrected path-length estimates. Such an example method is described further herein with regard to FIG. 4.

In examples wherein the detector inefficiencies are dynamic yet identifiable at the point of measurement (e.g., dynamically low-performance detector elements), method 300 may obtain the corrected path-length estimates differently depending on whether the forward model and the correction function are linear or nonlinear. For example, if the forward model f and the correction function $g_\Omega$ are at least approximately linear, method 300 may generate a forward model based on the calibration data, convert the imaging data to estimated path lengths with the inverse of the forward model, and apply the correction function to the estimated path lengths to generate the corrected path-length estimates. Such an example method is described further herein with regard to FIG. 5.

As another example, if the forward model f and the correction function $g_\Omega$ are nonlinear, method 300 may dynamically generate the forward model after determining the correction function $g_\Omega$ as well as how the correction function $g_\Omega$ is applied to the measured imaging data. For example, method 300 may select a correction function $g_\Omega$ for each detector element based on the acquired imaging data, apply the correction function $g_\Omega$ to the calibration data, generate a corrected forward model based on the corrected calibration data, apply the correction function $g_\Omega$ to the imaging data, and convert the corrected imaging data to corrected path-length estimates with the inverse of the corrected forward model. Such an example method for dynamic and nonlinear corrections is described further herein with regard to FIG. 6.

After obtaining the corrected path-length estimates, method 300 continues to 325. At 325, method 300 reconstructs material density image(s) based on the corrected path-length estimates. The corrected path-length estimates generated at 320 comprise material-basis projections described hereinabove. The corrected path-length estimates may therefore be reconstructed to form a pair or a set of material-density maps or images comprising each respective basis material, such as bone, soft tissue, and/or contrast agent maps. The density maps or images may be, in turn, associated to form a volume rendering of the basis material, for example, bone, soft tissue, and/or contrast agent, in the imaged volume. Once reconstructed, the basis material image or material density images reveal internal features of the imaging subject, expressed in the densities of basis materials.

At 330, method 300 outputs the reconstructed material density images. As an illustrative and non-limiting example, method 300 may output the reconstructed material density images to the display device 232 for displaying the reconstructed material density images to the user of the imaging system 200. Additionally or alternatively, method 300 may output the reconstructed material density images to the PACS 224 for remote storage and review, and/or to mass storage 218 for storage. Furthermore, the basis materials maps or images may be combined to generate additional images, e.g., mono-energetic images which emulate an acquisition using an x-ray source emitting photons at a single energy, to aid diagnostic purposes. Method 300 then returns.

Figure 4:
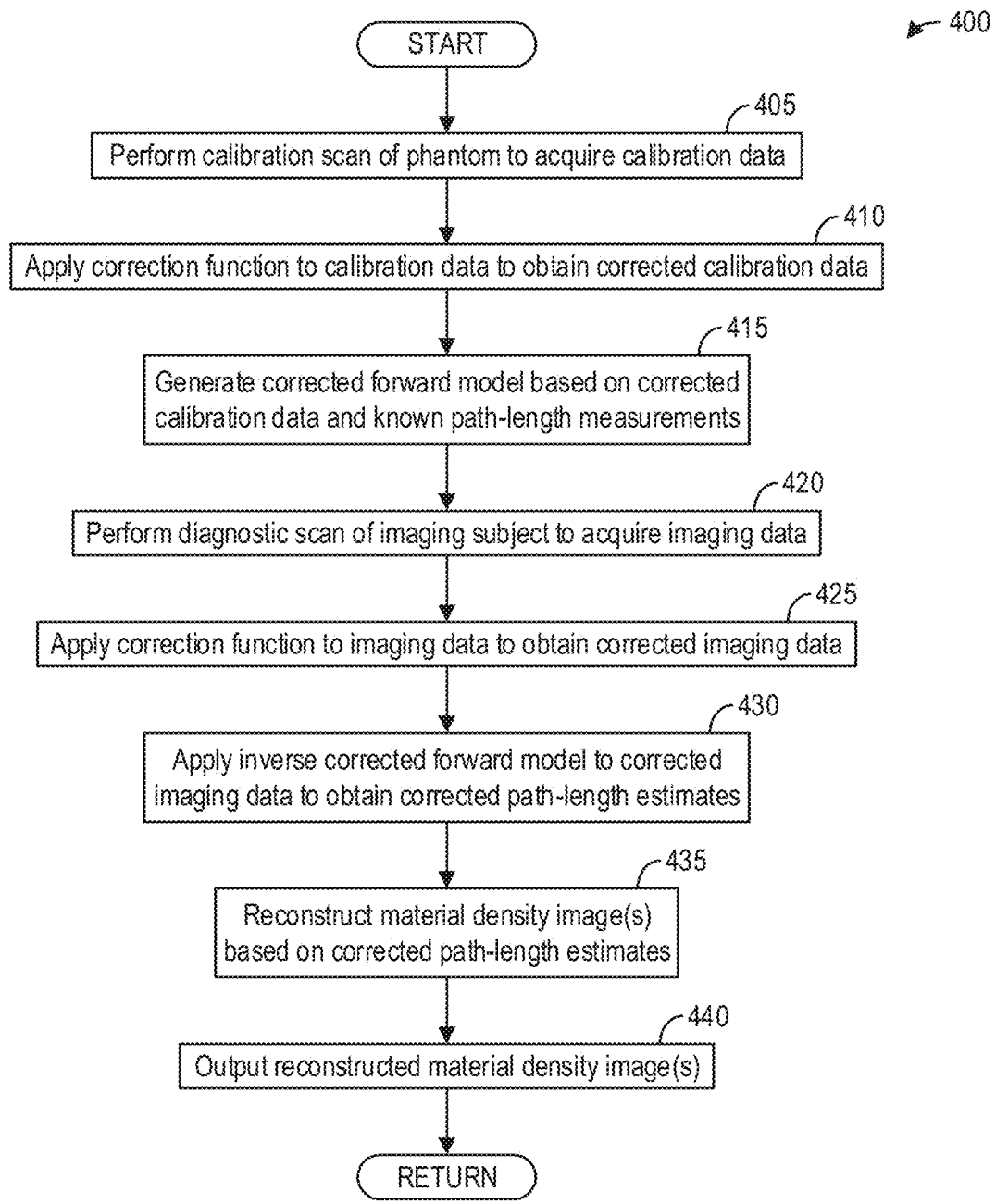
FIG. 4 shows a high-level flow chart illustrating an example method for material decomposition with predetermined corrections to improve spectral fidelity, according to an embodiment.

FIG. 4 shows a high-level flow chart illustrating an example method 400 for material decomposition with predetermined corrections to improve spectral fidelity, according to an embodiment. In particular, method 400 relates to improving spectral fidelity for persistent issues with detector design or certain detector elements. Method 400 is described with regard to the systems and components of FIGS. 1 and 2, though it should be appreciated that method 400 may be implemented with other systems and components without departing from the scope of the present disclosure. Method 400 may be implemented as executable instructions in the non-transitory memory of the computing device 216 and/or the image reconstructor 230, for example, and may be executed by the computing device 216 and/or the image reconstructor 230 to perform the actions described herein.

Method 400 begins at 405. At 405, method 400 performs a calibration scan of a phantom to acquire normalized calibration data I. For example, method 400 may control the x-ray source 104 via the x-ray controller 210 to generate an x-ray radiation beam 106 toward a phantom with a known material composition and a known, precise geometry, and further may acquire, via the DAS 214, projection data corresponding to the detected photons measured or counted by the detector elements 202 of the detector array 108. Data may also be acquired when the phantom is removed from the x-ray radiation beam 106 for normalization purposes. As the material composition and geometry of the phantom is known, the projection data thus acquired comprises calibration data for identifying the spectral characteristics and performance of the detector elements 202, for example.

At 410, method 400 applies a correction function to the calibration data to obtain corrected calibration data. In particular, as the problem being addressed is a function of the detector design and is repeatable between detectors, the correction function $g_\Omega$ for each detector element 202 is predefined and may be applied to the calibration data I to obtain corrected calibration data $\tilde{I}$:

$$\tilde{I}=g_\Omega(I).$$

After obtaining the corrected calibration data $\tilde{I}$, method 400 continues to 415. At 415, method 400 generates a corrected forward model $\tilde{f}$ based on the corrected calibration data $\tilde{I}$ and known path-length measurements A, such that:

$$\tilde{f}(A)=\tilde{I}.$$

Continuing at 420, method 400 performs a diagnostic scan of the imaging subject to acquire imaging data. For example, method 400 may control the x-ray source 104 via the x-ray controller 210 to generate an x-ray radiation beam 106 towards an imaging subject, such as the subject 204, with an unknown material composition and an unknown geometry, and further may acquire, via the DAS 214, projection data corresponding to the detected photons measured or counted by the detector elements 202 of the detector array 108. The imaging data comprises the projection data thus acquired. It should be appreciated that the diagnostic scan may be performed before generating the corrected calibration data and the corrected forward model at 410 and 415, respectively, and that the diagnostic scan is depicted as occurring afterwards to emphasize that the correction function is predetermined without knowledge of the imaging data acquired during the diagnostic scan.

At 425, method 400 applies the correction function $g_\Omega$ to the imaging data to obtain corrected imaging data. In particular, the correction function $g_\Omega$ for each detector element is applied to the imaging data $I_r$ from each corresponding detector element, similar to how the correction function $g_\Omega$ was applied to the calibration data at 410, to obtain the corrected imaging data $\tilde{I}_r$:

$$\tilde{I}_r=g_\Omega(I_r).$$

After obtaining the corrected imaging data, method 400 continues to 430. At 430, method 400 applies the inverse of the corrected forward model $\tilde{f}$ to the corrected imaging data $\tilde{I}_r$ to obtain corrected path-length estimates $\tilde{A}_r$:

$$\tilde{A}_r=\tilde{f}^{-1}(\tilde{I}_r).$$

Once the corrected path-length estimates $\tilde{A}_r$ are obtained, method 400 continues to 435. At 435, method 400 reconstructs material density image(s) based on the corrected path-length estimates. For example, method 400 may reconstruct the corrected path-length estimates, for example using filtered backprojection or another reconstruction technique, to form a pair or a set of material-density maps or images comprising each respective basis material, such as bone, soft tissue, and/or contrast agent maps. The density maps or images may be, in turn, associated to form a volume rendering of the basis material, for example, bone, soft tissue, and/or contrast agent, in the imaged volume. Once reconstructed, the basis material image or material density images reveal internal features of the imaging subject, expressed in the densities of basis materials.

At 440, method 400 outputs the reconstructed material density image(s). As an illustrative and non-limiting example, method 400 may output the reconstructed material density images to the display device 232 for displaying the reconstructed material density images to the user of the imaging system 200. Additionally or alternatively, method 400 may output the reconstructed material density images to the PACS 224 for remote storage and review, and/or to mass storage 218 for storage. Furthermore, the basis materials maps or images may be combined to generate additional images, e.g., mono-energetic images which emulate an acquisition using an x-ray source emitting photons at a single energy, to aid diagnostic purposes. Method 400 then returns.

Figure 5:
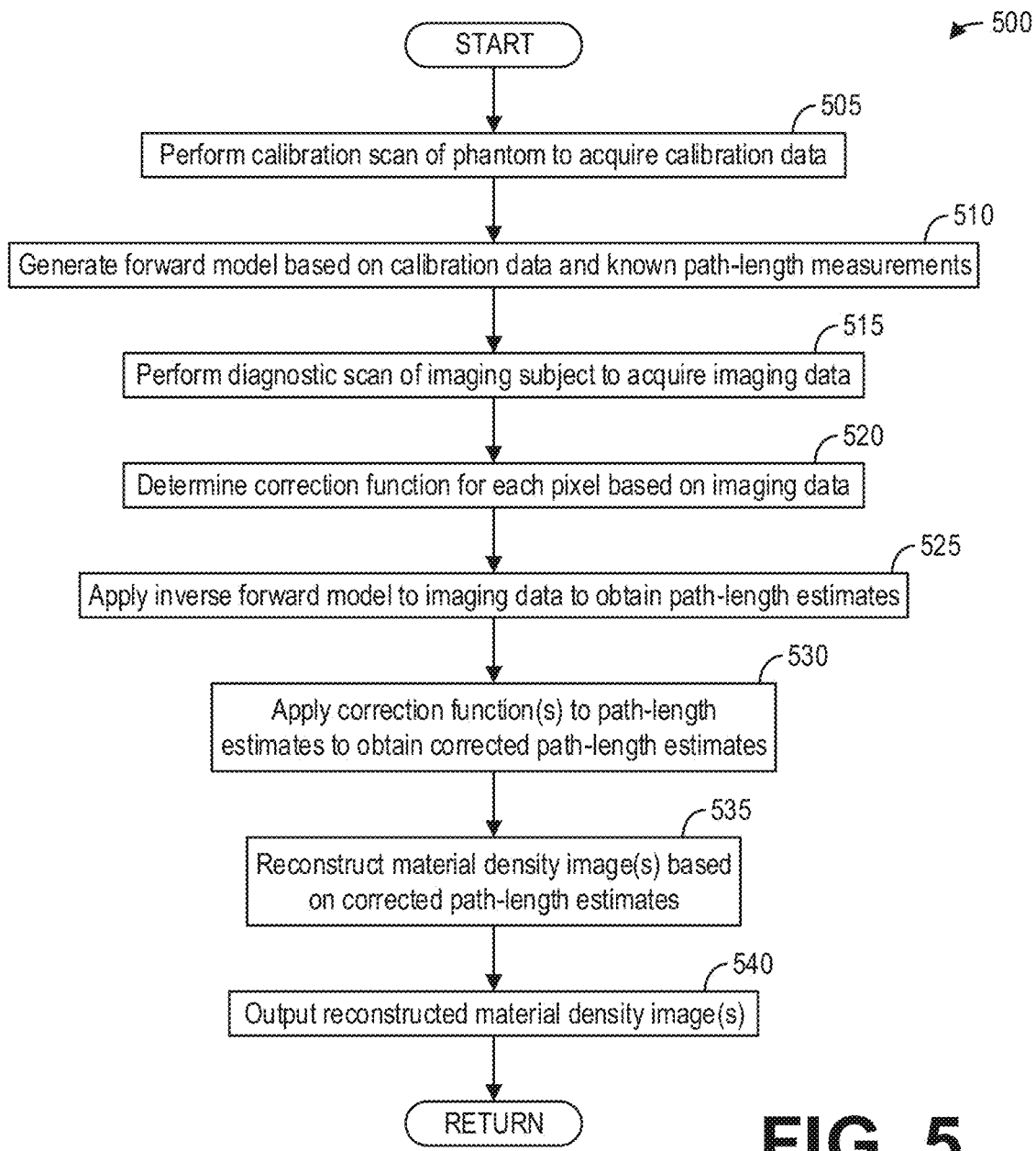
FIG. 5 shows a high-level flow chart illustrating an example method for material decomposition with dynamic linear corrections to improve spectral fidelity, according to an embodiment.

FIG. 5 shows a high-level flow chart illustrating an example method 500 for material decomposition with dynamic linear corrections to improve spectral fidelity, according to an embodiment. In particular, method 500 relates to improving spectral fidelity for dynamic detector efficiency issues identifiable at the point of measurement when the forward model f and the correction function $g_\Omega$ are at least approximately linear. Method 500 is described with regard to the systems and components of FIGS. 1 and 2, though it should be appreciated that method 500 may be implemented with other systems and components without departing from the scope of the present disclosure. Method 500 may be implemented as executable instructions in the non-transitory memory of the computing device 216 and/or the image reconstructor 230, for example, and may be executed by the computing device 216 and/or the image reconstructor 230 to perform the actions described herein.

Method 500 begins at 505. At 505, method 500 performs a calibration scan of a phantom to acquire calibration data. For example, method 500 may control the x-ray source 104 via the x-ray controller 210 to generate an x-ray radiation beam 106 toward a phantom with a known material composition and a known, precise geometry, and further may acquire, via the DAS 214, projection data corresponding to the detected photons measured or counted by the detector elements 202 of the detector array 108. Data may also be acquired when the phantom is removed from the x-ray radiation beam 106 for normalization purposes. As the material composition and geometry of the phantom is known, the projection data thus acquired comprises calibration data for identifying the spectral characteristics and performance of the detector elements 202, for example.

At 510, method 500 generates a forward model based on the calibration data and known path-length measurements of the phantom. For example, method 500 may generate a forward model f based on the calibration data I and known path-length measurements A of the phantom, such that:

$$f(A)=I.$$

Continuing at 515, method 500 performs a diagnostic scan of the imaging subject to acquire imaging data. For example, method 500 may control the x-ray source 104 via the x-ray controller 210 to generate an x-ray radiation beam 106 towards an imaging subject, such as the subject 204, with an unknown material composition and an unknown geometry, and further may acquire, via the DAS 214, projection data corresponding to the detected photons measured or counted by the detector elements 202 of the detector array 108. The imaging data thus comprises the projection data acquired during the diagnostic scan.

After acquiring the imaging data at 515, method 500 continues to 520. At 520, method 500 determines a correction function for each pixel based on the imaging data. In particular, method 500 evaluates data conditions of the imaging data and selects a correction function $g_\Omega$ for each detector element based on the data conditions as described hereinabove with regard to FIG. 3. In this way, the correction function(s) are dynamic or may vary from scan to scan in accordance with the dynamic spectral behavior of the detector array 108. The correction function(s) selected are linear or at least are approximately linear.

Continuing at 525, method 500 applies an inverse of the forward model generated at 510 to the imaging data acquired at 515 to obtain estimated path-length measurements. For example, method 500 may apply an inverse of the forward model f to the imaging data $I_r$ to obtain path-length estimates $A_r$, such that:

$$A_r = f^{-1}(I_r).$$

With the path-length estimates for the acquired imaging data thus obtained, method 500 continues to 530. At 530, method 500 applies the correction function(s) determined at 520 to the path-length estimates $A_r$ to obtain corrected path-length estimates $\tilde{A}_r$:

$$\tilde{A}_r = g_\Omega(A_r).$$

Thus, the linearity of the forward model f and the linearity of the correction function $g_\Omega$ allows the spectral fidelity to be enhanced by applying the correction function $g_\Omega$ to the path-length estimates $A_r$, rather than applying the correction function $g_\Omega$ directly to the calibration data or the imaging data.

At 535, method 500 reconstructs material density image (s) based on the corrected path-length estimates $\tilde{A}_r$. For example, method 500 may reconstruct the corrected path-length estimates $\tilde{A}_r$, for example using filtered backprojection or another reconstruction technique, to form a pair or a set of material-density maps or images comprising each respective basis material, such as bone, soft tissue, and/or contrast agent maps. The density maps or images may be, in turn, associated to form a volume rendering of the basis material, for example, bone, soft tissue, and/or contrast agent, in the imaged volume. Once reconstructed, the basis material image or material density images reveal internal features of the imaging subject, expressed in the densities of basis materials.

Continuing at 540, method 500 outputs the reconstructed material density image(s). As an illustrative and non-limiting example, method 500 may output the reconstructed material density images to the display device 232 for displaying the reconstructed material density images to the user of the imaging system 200. Additionally or alternatively, method 500 may output the reconstructed material density images to the PACS 224 for remote storage and review, and/or to mass storage 218 for storage. Furthermore, the basis materials maps or images may be combined to generate additional images, e.g., mono-energetic images which emulate an acquisition using an x-ray source emitting photons at a single energy, to aid diagnostic purposes. Method 500 then returns.

Figure 6:
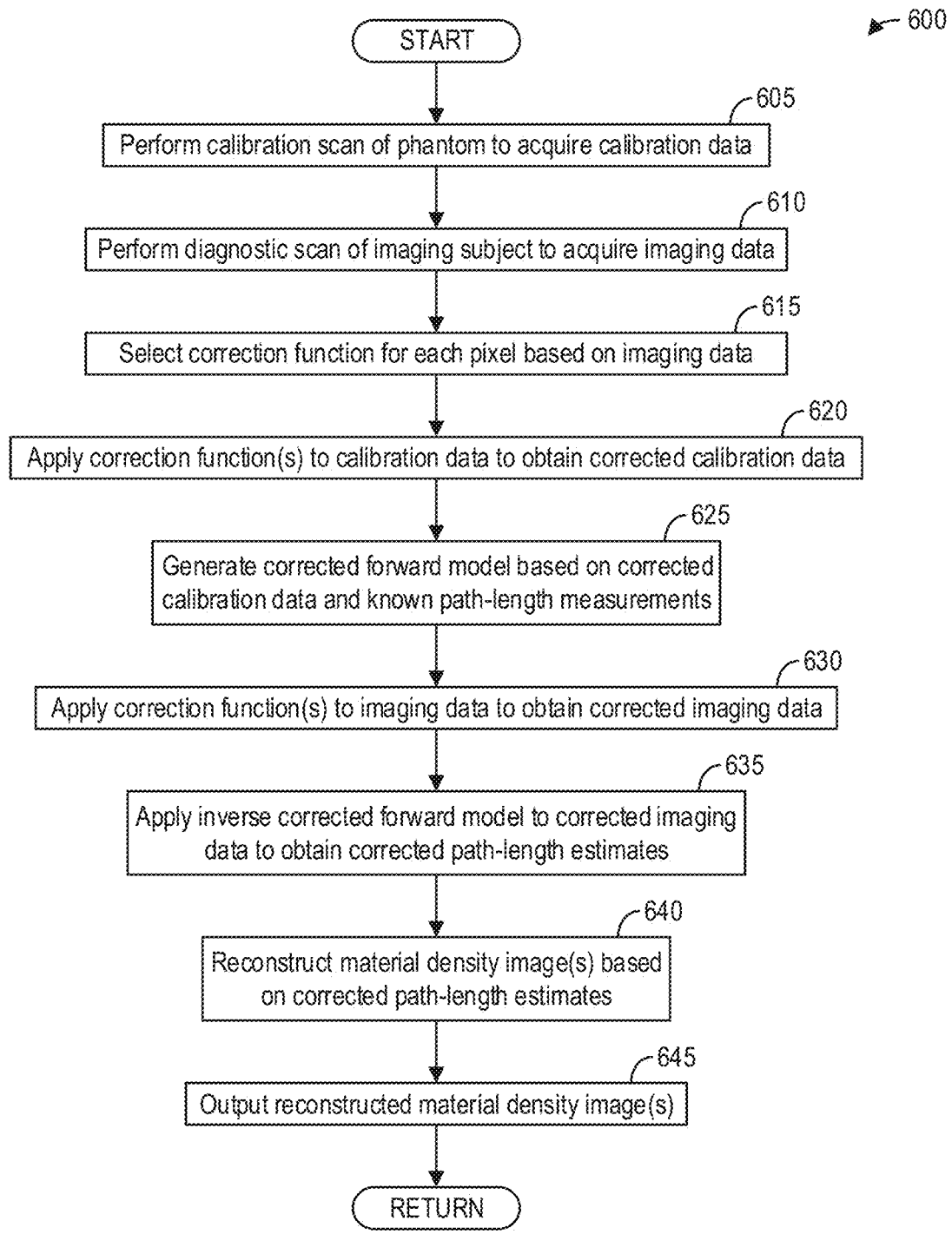
FIG. 6 shows a high-level flow chart illustrating an example method for material decomposition with dynamic nonlinear corrections to improve spectral fidelity, according to an embodiment.

FIG. 6 shows a high-level flow chart illustrating an example method 600 for material decomposition with dynamic nonlinear corrections to improve spectral fidelity, according to an embodiment. In particular, method 600 relates to improving spectral fidelity for dynamic detector efficiency issues identifiable at the point of measurement when the forward model f and the correction function $g_\Omega$ are nonlinear. Method 600 is described with regard to the systems and components of FIGS. 1 and 2, though it should be appreciated that method 600 may be implemented with other systems and components without departing from the scope of the present disclosure. Method 600 may be implemented as executable instructions in the non-transitory memory of the computing device 216 and/or the image reconstructor 230, for example, and may be executed by the computing device 216 and/or the image reconstructor 230 to perform the actions described herein.

Method 600 begins at 605. At 605, method 600 performs a calibration scan of a phantom to acquire calibration data. For example, method 600 may control the x-ray source 104 via the x-ray controller 210 to generate an x-ray radiation beam 106 toward a phantom with a known material composition and a known, precise geometry, and further may acquire, via the DAS 214, projection data corresponding to the detected photons measured or counted by the detector elements 202 of the detector array 108. Data may also be acquired when the phantom is removed from the x-ray radiation beam 106 for normalization purposes. As the material composition and geometry of the phantom is known, the projection data thus acquired comprises calibration data for identifying the spectral characteristics and performance of the detector elements 202, for example.

At 610, method 600 performs a diagnostic scan of an imaging subject to acquire imaging data. For example, method 600 may control the x-ray source 104 via the x-ray controller 210 to generate an x-ray radiation beam 106 towards an imaging subject, such as the subject 204, with an unknown material composition and an unknown geometry, and further may acquire, via the DAS 214, projection data corresponding to the detected photons measured or counted by the detector elements 202 of the detector array 108. The imaging data comprises the projection data thus acquired.

At 615, method 600 selects a correction function for each detector pixel or detector element 202 based on the imaging data. For example, method 600 evaluates data conditions of the imaging data and selects a correction function $g_\Omega$ for each detector element 202 based on the data conditions as described hereinabove with regard to FIG. 3. In this way, the correction function(s) are dynamic or may vary from scan to scan or even from detector pixel to detector pixel within a view in a scan, in accordance with the dynamic spectral behavior of the detector array 108. The correction function (s) selected are nonlinear, in contrast with the correction function(s) of method 500 described hereinabove.

With the correction functions dynamically selected, method 600 continues to 620. At 620, method 600 applies the correction functions to the calibration data acquired at 605 to obtain corrected calibration data. For example, method 600 may apply the correction functions $g_\Omega$ to the calibration data I acquired at 605 to obtain corrected calibration data $\tilde{I}$:

$$\tilde{I} = g_\Omega(I).$$

Continuing at 625, method 600 generates a corrected forward model based on the corrected calibration data and the known path-length measurements of the phantom. For example, method 600 may generate a corrected forward model $\tilde{f}$ based on the corrected calibration data $\tilde{I}$ and the known path-length measurements A, such that:

$$\tilde{f}(A) = \tilde{I}.$$

In this way, the calibration technique is updated to account for dynamic nonlinear spectral deficiencies of the detector elements 202.

Continuing at 630, method 600 applies the correction function(s) to the imaging data to obtain corrected imaging data. For example, method 600 may apply the correction functions $g_\Omega$ to the imaging data $I_r$ acquired at 610 to obtain corrected imaging data $\tilde{I}_r$:

$$\tilde{I}_r = g_\Omega(I_r).$$

Continuing at 635, method 600 applies the inverse of the corrected forward model to the corrected imaging data to obtain corrected path-length estimates. For example, method 600 may apply the inverse of the corrected forward model $\tilde{f}$ to the corrected imaging data $\tilde{I}_r$ to obtain corrected path-length estimates $\tilde{A}_r$:

$$\tilde{A}_r = \tilde{f}^{-1}(\tilde{I}_r)$$

At 640, method 600 reconstructs material density image (s) based on the corrected path-length estimates. For example, method 600 may reconstruct the corrected path-length estimates, for example using filtered backprojection or another reconstruction technique, to form a pair or a set of material-density maps or images comprising respective basis material, such as bone, soft tissue, and/or contrast agent maps. The density maps or images may be, in turn, associated to form a volume rendering of the basis material, for example, bone, soft tissue, and/or contrast agent, in the imaged volume. Once reconstructed, the basis material image or material density images reveal internal features of the imaging subject, expressed in the densities of basis materials.

Continuing at 645, method 600 outputs the reconstructed material density image(s). As an illustrative and non-limiting example, method 600 may output the reconstructed material density images to the display device 232 for displaying the reconstructed material density images to the user of the imaging system 200. Additionally or alternatively, method 600 may output the reconstructed material density images to the PACS 224 for remote storage and review, and/or to mass storage 218 for storage. Furthermore, the basis materials maps or images may be combined to generate additional images, e.g., mono-energetic images which emulate an acquisition using an x-ray source emitting photons at a single energy, to aid diagnostic purposes. Method 600 then returns.

Thus, various systems and methods are provided for improving spectral fidelity for material decomposition. The fidelity of spectral information is crucial for the success of photon-counting systems. The techniques provided herein enable the maintenance of spectral information when other data processing is applied which could contaminate the spectral characteristics. Moreover, these techniques are broadly applicable to correction of similar measurements in all types of photon-counting systems where data fidelity has been degraded, in terms of SNR or spectral content, by low-performing detector pixels or detector pixels with low detection efficiency. An alternative approach to solving the issues addressed herein may include modeling all physical effects in the forward model f and attempting to invert the forward model f by some iterative means. However, such an approach would be computationally expensive and highly ill-posed, as a substantial amount of prior information may be required to maintain the stability of the inversion. The techniques of the present disclosure thus provide substantial advantages over such an approach.

The formalism and the generality of the calibration and correction methods are thus outlined hereinabove. As an example for how to apply such an approach to a real problem, consider a CT imaging system exhibiting a fixed pattern of low-efficiency detector regions. This fixed pattern may be designed to facilitate manufacturing processes, for example. To reconcile the loss of efficiency in such regions, an appropriate correction function $g_\Omega$ may be applied to the measurements. One approach to a correction function $g_\Omega$ may include pooling the neighbors of pixels below a certain efficiency threshold. The implementation of such a correction scheme may boost the counts for the regions of low efficiency, thereby providing an increase in overall signal for low detection efficiency regions. The correction function $g_\Omega$ may be predetermined as described hereinabove with regard to FIG. 4, and the calibration forward model f can be created based on the corrected calibration counts prior to the acquisition or collection of clinical imaging data. While the correction function $g_\Omega$ may comprise a pooling kernel as mentioned above, with an appropriate increase in the signal of the low-efficiency detector elements, tuning of the pooling method or the adoption of other correction methods may be prudent for overall image quality enhancement.

Other approaches include, as illustrative and non-limiting examples, using a domain $\Omega$ of measurements across rows, columns, and views, if appropriate, that contain pixels that have similar spectral-detection characteristics and employing standard interpolation methods (e.g., linear, quadratic, and so on). In this way, the material decomposition process may be unaltered from the mappings or forward models determined during processing of the calibration measurements. Another approach may include using a domain $\Omega$ of measurements across rows, columns, and views, if appropriate, that contain pixels that have differing spectral-detection characteristics and employing standard interpolation methods (e.g., linear, quadratic, and so on). In this way, the mapping from intensity measurements to material path lengths should be updated as described hereinabove with regard to FIGS. 4 and 6, for example, considering the modified spectral performance of the interpolated detector element. The updated mappings or forward models may be computed a priori if the locales of the low-performing detector elements are known before the diagnostic scan or may be modified dynamically as determined by the measurements acquired during or between diagnostic scans.

Further, while the methods provided hereinabove include performing a calibration scan of a phantom to acquire calibration data which may be used to generate a forward model for converting the imaging data to path-length estimates, it should be appreciated that in some examples, the methods may not include performing such a calibration scan. For example, modeling and simulation of the system behavior may be used to construct a forward model and/or to simulate the calibration data for constructing the forward model.

As an illustrative example of the correction methods provided herein, FIGS. 7-9 depict example results obtained with a 40-centimeter water phantom. In particular, FIG. 7 shows an example image 700 exhibiting ring artifacts due to low-efficiency pixels, with no correction applied. FIG. 8 shows an example image 800 with low-efficiency pixel correction applied to the projection data, but without a corresponding modeling in the spectral forward model f. For example, correction function(s) are applied to the signals from the detector elements to obtain corrected projection data or corrected imaging data, but the forward model f is not updated or corrected. FIG. 9 shows an example image 900 with low-efficiency pixel correction and corrected spectral forward modeling. That is, the image 900 is obtained in accordance with the method of FIG. 6, as an example, wherein correction function(s) are applied to the projection data and a corrected forward model f is used to convert the corrected projection data.

As depicted, ring artifacts are clearly visible in the image 700 as well as the image 800, despite the low-efficiency detector pixel correction for the image 800. The ring artifacts are substantially eliminated in the image 900 due to the updated forward modeling applied.

To further illustrate the ring artifacts in the images 700 and 800 as well as the relative impact of the correction methods provided herein, FIGS. 10 and 11 show graphs comparing the images 700, 800, and 900. In particular, FIG. 10 shows a graph 1000 illustrating azimuthally-averaged radial profiles from reconstructed data to compare the uncorrected image 700 and the partially-corrected image 800, while FIG. 11 shows a graph 1100 illustrating azimuthally-averaged radial profiles from reconstructed data to compare the uncorrected image 700 and the fully-corrected image 900. The graph 1000 includes a radial profile 1005 for the uncorrected image 700 as well as a radial profile 1010 for the partially-corrected image 800, while the graph 1100 includes the radial profile 1005 as well as a radial profile 1115 for the fully-corrected image 900. The graphs 1000 and 1100 depict the Hounsfield units (HU) for each image as a function of radius, measured in millimeters, from the center of the phantom (0 mm) to the edge of the phantom (200 mm).

As shown in the radial profile 1005 for the uncorrected image 700, the peaks indicate the positions of ring artifacts in the image 700. As shown in the radial profile 1010 for the partially-corrected image 800, many peaks are even higher than the peaks of the radial profile 1005, thereby indicating that the partially-corrected image 800 exhibits stronger ring artifacts than the uncorrected image 700. Notably, the radial profile 1010 at a radius of 5 mm exhibits an HU range from approximately 994 HU to 1015 HU, with an HU change of over 20 HU, whereas the HU range for the radial profile 1005 in the same region is 997 HU to 1013 HU, with an overall HU change of 16 HU. That is, rather than increasing the spectral fidelity of the acquired signal, applying corrections to the acquired signal without further updating the forward model or otherwise ensuring that the fidelity is enhanced downstream in the processing chain results in potentially worse fidelity than leaving the projection data uncorrected.

In contrast, the approaches provided herein when applied to the projection data result in a substantially better image quality. In particular, as shown in the radial profile 1115 for the fully-corrected image 900, all peaks in the radial profile 1115 are substantially reduced relative to the radial profile 1005 for the uncorrected image 700. Referring to the largest peak in the radial profile 1115 near the radius of 5 mm, the HU range extends from 999 HU to 1009 HU, with an overall HU change of 10 HU. This HU variation is hardly noticeable in the central region of the image 900. Thus, the correction techniques provided herein largely improve the spectral fidelity of the low-performance detector elements used to acquire the projection data in the depicted example.

A technical effect of the disclosure includes the increased spectral fidelity for material decomposition in CT imaging. Another technical effect of the disclosure includes the reduction of image artifacts caused by under-performing or low-efficiency detector elements. Another technical effect of the disclosure includes the increase of image quality for material density images acquired with photon-counting detectors. Yet another technical effect of the disclosure is the improvement of photon-counting detectors for quantitative medical imaging. Another technical effect of the disclosure includes the reduction of dose for photon-counting detectors with an increased image quality. Another technical effect of the disclosure includes the correction of spectral forward models for basis material decomposition.

Thus, various systems and methods for improving spectral fidelity for material decomposition are provided. In one embodiment, a method comprises performing a scan of a subject to acquire, with a detector array comprising a plurality of detector elements, projection data of the subject, generating corrected path-length estimates based on the projection data and one or more selected correction functions, and reconstructing at least one material density image based on the corrected path-length estimates. In a first example of the method, the method further comprises performing a calibration scan of a phantom to acquire, with the detector array, calibration data. In a second example of the method optionally including the first example, the method further comprises applying the one or more selected correction functions to the calibration data to generate corrected calibration data, and generating a corrected forward model based on the corrected calibration data and known material composition and geometry of the phantom. In a third example of the method optionally including one or more of the first and second examples, generating the corrected path-length estimates comprises applying the one or more selected correction functions to the projection data to generate corrected projection data, and converting the corrected projection data to the corrected path-length estimates with the corrected forward model. In a fourth example of the method optionally including one or more of the first through third examples, the method further comprises selecting the one or more selected correction functions prior to performing the calibration scan and the diagnostic scan of a subject based on known efficiency and performance issues with one or more detector elements of the plurality of detector elements. In a fifth example of the method optionally including one or more of the first through fourth examples, the method further comprises selecting the one or more selected correction functions based on dynamic efficiency or performance issues with one or more detector elements of the plurality of detector elements identified in the projection data. In a sixth example of the method optionally including one or more of the first through fifth examples, the method further comprises generating a forward model based on the calibration data and known material composition and geometry of the phantom, and converting the projection data to path-length estimates with the forward model, wherein generating the corrected path-length estimates comprises applying the one or more selected correction functions to the path-length estimates to generate the corrected path-length estimates. In a seventh example of the method optionally including one or more of the first through sixth examples, one or more of the one or more correction functions and the forward model are linear, and the one or more correction functions are selected based on deficiencies of one or more detector elements of the plurality of detector elements identified in the projection data. In an eighth example of the method optionally including one or more of the first through seventh examples, the method further comprises outputting the at least one material density image to a display device for display. In a ninth example of the method optionally including one or more of the first through eighth examples, the one or more selected correction functions comprise one or more of a spatial interpolation filter, a temporal interpolation filter, a view interpolation filter, and a spectral interpolation filter.

In another embodiment, a method comprises performing a calibration scan of a phantom to acquire, with a detector array comprising a plurality of detector elements, calibration data, performing a diagnostic scan of a subject to acquire, with the detector array, projection data, generating corrected path-length estimates from the projection data based on one or more selected correction functions and a forward model generated from the calibration data, and reconstructing at least one material density image based on the corrected path-length estimates.

In a first example of the method, the method further comprises applying the one or more selected correction functions to the calibration data to generate corrected calibration data, and generating the forward model from the corrected calibration data and known material composition and geometry of the phantom, wherein generating the corrected path-length estimates from the projection data comprises applying the one or more selected correction functions to the projection data to generate corrected projection data, and converting the corrected projection data with the forward model to generate the corrected path-length estimates. In a second example of the method optionally including the first example, the method further comprises selecting the one or more selected correction functions prior to acquiring the calibration scan and the diagnostic scan of a subject based on known efficiency and performance issues with one or more detector elements of the plurality of detector elements, or selecting the one or more selected correction functions based on dynamic efficiency or performance issues with one or more detector elements of the plurality of detector elements identified in the projection data. In a third example of the method optionally including one or more of the first and second examples, generating the corrected path-length estimates from the projection data comprises converting the projection data with the forward model to generate path-length estimates, and applying the one or more selected correction functions to the path-length estimates to generate the corrected path-length estimates.

In yet another embodiment, a system comprises an x-ray source configured to generate a beam of x-rays towards a subject; a detector array comprising a plurality of detector elements configured to detect the beam of x-rays attenuated by the subject; and a computing device communicatively coupled to the x-ray source and the detector array, the computing device configured with instructions in non-transitory memory that when executed cause the computing device to: control the x-ray source and the detector array to scan the subject and acquire projection data; generate corrected path-length estimates based on the projection data and one or more selected correction functions; and reconstruct at least one material density image based on the corrected path-length estimates.

In a first example of the system, the computing device is further configured with instructions in non-transitory memory that when executed cause the computing device to control the x-ray source and the detector array to scan a phantom to acquire calibration data, apply the one or more selected correction functions to the calibration data to generate corrected calibration data, and generate a corrected forward model based on the corrected calibration data and known material composition and geometry of the phantom. In a second example of the system optionally including the first example, the computing device is further configured with instructions in non-transitory memory that when executed cause the computing device to apply the one or more selected correction functions to the projection data to generate corrected projection data, and convert the corrected projection data with the corrected forward model to generate the corrected path-length estimates. In a third example of the system optionally including one or more of the first and second examples, the one or more selected correction functions are selected from a library of correction functions based on predetermined or dynamically-determined spectral fidelity issues of the plurality of detector elements, the library of correction functions including one or more of a spatial interpolation filter, a temporal interpolation filter, a view interpolation filter, and a spectral interpolation filter. In a fourth example of the system optionally including one or more of the first through third examples, each detector element of the plurality of detector elements comprises a photon-counting detector element. In a fifth example of the system optionally including one or more of the first through fourth examples, the system further comprises a display device communicatively coupled to the computing device, and the computing device is further configured with instructions in non-transitory memory that when executed cause the computing device to output the at least one material density image to the display device for display.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
    performing a scan of a subject to acquire, with a detector array comprising a plurality of detector elements, projection data of the subject;
    generating corrected path-length estimates based on the projection data and one or more selected correction functions; and
    reconstructing at least one material density image based on the corrected path-length estimates.

2. The method of claim 1, further comprising performing one or more of a calibration scan of a phantom to acquire, with the detector array, calibration data, and modeling system behavior of the detector array to simulate the calibration data.

3. The method of claim 2, further comprising applying the one or more selected correction functions to the calibration data to generate corrected calibration data, and generating a corrected forward model based on the corrected calibration data and known material composition and geometry of the phantom.

4. The method of claim 3, wherein generating the corrected path-length estimates comprises applying the one or more selected correction functions to the projection data to generate corrected projection data, and converting the corrected projection data to the corrected path-length estimates with the corrected forward model.

5. The method of claim 4, further comprising selecting the one or more selected correction functions prior to performing the calibration scan and the scan of the subject based on known efficiency and performance issues with one or more detector elements of the plurality of detector elements.

6. The method of claim 4, further comprising selecting the one or more selected correction functions based on dynamic efficiency or performance issues with one or more detector elements of the plurality of detector elements identified in the projection data.

7. The method of claim 2, further comprising generating a forward model based on the calibration data and known material composition and geometry of the phantom, and converting the projection data to path-length estimates with the forward model, wherein generating the corrected path-length estimates comprises applying the one or more selected correction functions to the path-length estimates to generate the corrected path-length estimates.

8. The method of claim 7, wherein one or more of the one or more correction functions and the forward model are linear, and wherein the one or more correction functions are selected based on deficiencies of one or more detector elements of the plurality of detector elements identified in the projection data.

9. The method of claim 1, further comprising outputting one or more of the at least one material density image and combinations thereof to a display device for display, wherein each detector element of the plurality of detector elements comprises a photon-counting detector element, and wherein a correction function is selected for each detector element, such that different correction functions are applied to different detector elements.

10. The method of claim 1, wherein the one or more selected correction functions comprise one or more of a spatial interpolation filter, a temporal interpolation filter, a view interpolation filter, and a spectral interpolation filter.

11. A method, comprising:
    performing a calibration scan of a phantom to acquire, with a detector array comprising a plurality of detector elements, calibration data;
    performing a diagnostic scan of a subject to acquire, with the detector array, projection data;
    applying one or more selected correction functions to the calibration data to generate corrected calibration data;
    generating a corrected forward model from the corrected calibration data and known material composition and geometry of the phantom;
    generating corrected path-length estimates from the projection data based on the one or more selected correction functions and the corrected forward model; and
    reconstructing at least one material density image based on the corrected path-length estimates.

12. The method of claim 11, wherein generating the corrected path-length estimates from the projection data comprises applying the one or more selected correction functions to the projection data to generate corrected projection data, and converting the corrected projection data with the corrected forward model to generate the corrected path-length estimates.

13. The method of claim 11, further comprising selecting the one or more selected correction functions prior to acquiring the calibration scan and the diagnostic scan of a subject based on known efficiency and performance issues with one or more detector elements of the plurality of detector elements, or selecting the one or more selected correction functions based on dynamic efficiency or performance issues with one or more detector elements of the plurality of detector elements identified in the projection data.

14. The method of claim 11, wherein generating the corrected path-length estimates from the projection data comprises converting the projection data with the corrected forward model to generate path-length estimates, and applying the one or more selected correction functions to the path-length estimates to generate the corrected path-length estimates.

15. A system, comprising:
an x-ray source configured to generate a beam of x-rays towards a subject;
a detector array comprising a plurality of detector elements configured to detect the beam of x-rays attenuated by the subject;
a computing device communicatively coupled to the x-ray source and the detector array, the computing device configured with instructions in non-transitory memory that when executed cause the computing device to:
control the x-ray source and the detector array to scan the subject and acquire projection data;
generate corrected path-length estimates based on the projection data and one or more selected correction functions, the corrected path-length estimates generated with a corrected forward model, and wherein both the projection data and the forward model are corrected with the same calibration data; and
reconstruct at least one material density image based on the corrected path-length estimates.

16. The system of claim 15, wherein the computing device is further configured with instructions in non-transitory memory that when executed cause the computing device to control the x-ray source and the detector array to scan a phantom to acquire the calibration data, apply the one or more selected correction functions to the calibration data to generate corrected calibration data, and generate the corrected forward model based on the corrected calibration data and known material composition and geometry of the phantom.

17. The system of claim 16, wherein the computing device is further configured with instructions in non-transitory memory that when executed cause the computing device to apply the one or more selected correction functions to the projection data to generate corrected projection data, and convert the corrected projection data with the corrected forward model to generate the corrected path-length estimates.

18. The system of claim 15, wherein the one or more selected correction functions are selected from a library of correction functions based on predetermined or dynamically-determined spectral fidelity issues of the plurality of detector elements, the library of correction functions including one or more of a spatial interpolation filter, a temporal interpolation filter, a view interpolation filter, and a spectral interpolation filter.

19. The system of claim 15, wherein each detector element of the plurality of detector elements comprises a photon-counting detector element.

20. The system of claim 15, further comprising a display device communicatively coupled to the computing device, the computing device further configured with instructions in non-transitory memory that when executed cause the computing device to output one or more of the at least one material density image and combinations thereof to the display device for display.

* * * * *